US00PP35980P2

(12) United States Plant Patent
Mathey

(10) Patent No.: US PP35,980 P2
(45) Date of Patent: Jul. 9, 2024

(54) ***ABELIA* PLANT NAMED 'SMNAGBT'**

(50) Latin Name: ***Abelia* x *grandiflora***
Varietal Denomination: SMNAGBT

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/240,265

(22) Filed: Aug. 30, 2023

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226

CPC ... A01H 5/02; A01H 5/12; A01H 5/00; A01H 6/00

See application file for complete search history.

(56) References Cited

U.S. PATENT DOCUMENTS

PP20,568 P2 * 12/2009 Bronsther ..... Plt./226

* cited by examiner

*Primary Examiner* — June Hwu
(74) *Attorney, Agent, or Firm* — C. Anne Whealy

(57) ABSTRACT

A new and distinct cultivar of *Abelia* plant named 'SMNAGBT', characterized by its relatively compact, upright to outwardly spreading and mounding plant habit; vigorous growth habit and rapid growth rate; freely branching habit; dense and bushy appearance; developing leaves that are brownish orange in color and become green in color with development; freely and continuous flowering habit; large white-colored flowers that are tinged with light purple with light purple-colored throats; and good garden performance.

2 Drawing Sheets

Figure 1:
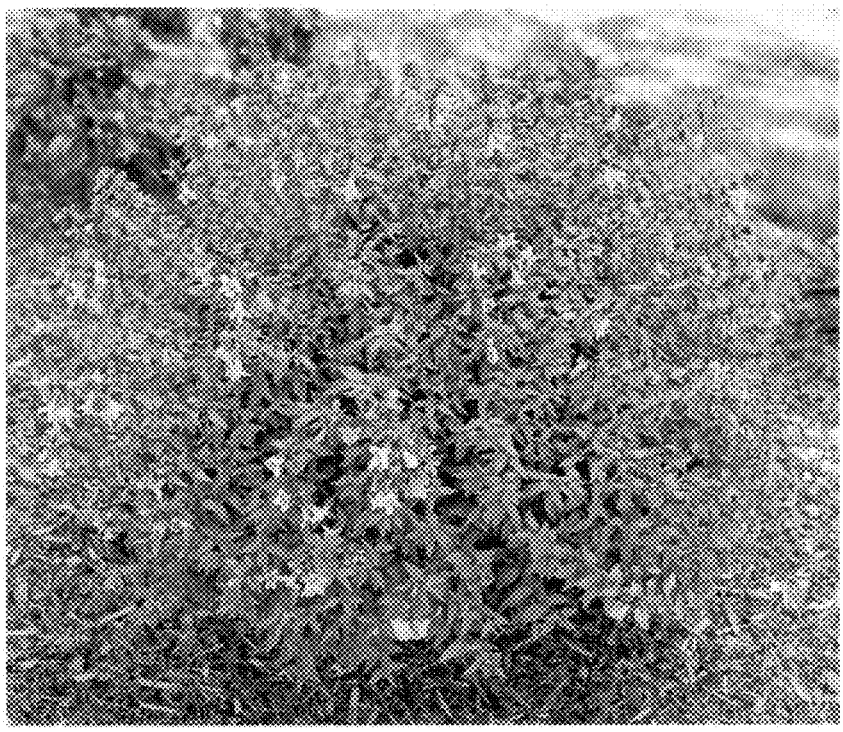

Botanical designation: *Abelia* x *grandiflora*.
Cultivar denomination: 'SMNAGBT'.

BACKGROUND OF THE INVENTION

The present invention relates to a new and distinct cultivar of *Abelia* plant, botanically known as *Abelia* x *grandiflora*, commonly referred to as Glossy *Abelia* and hereinafter referred to by the name 'SMNAGBT'.

The new *Abelia* is a product of a planned breeding program conducted by the Inventor in Grand Haven, Michigan. The objective of the breeding program was to develop new compact and freely flowering *Abelia* plants with attractive and unique leaf coloration.

The new *Abelia* plant originated from an open-pollination in 2018 of *Abelia* x *grandiflora* 'Bobbie', not patented, as the female, or seed parent with an unknown selection of *Abelia* x *grandiflora*. The new *Abelia* plant was discovered and selected by the Inventor in 2018 as a single flowering plant within the progeny of the stated open-pollination in a controlled environment in Grand Haven, Michigan.

Asexual reproduction of the new *Abelia* plant by softwood cuttings in a controlled greenhouse environment in Grand Haven, Michigan since 2019 has shown that the unique features of this new *Abelia* plant are stable and reproduced true to type in successive generations of asexual reproduction.

SUMMARY OF THE INVENTION

Plants of the new *Abelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNAGBT'. These characteristics in combination distinguish 'SMNAGBT' as a new and distinct *Abelia* plant:

1. Relatively compact, upright to outwardly spreading and mounding plant habit.
2. Vigorous growth habit and rapid growth rate.
3 Freely branching habit; dense and bushy appearance.
4. Developing leaves that are brownish orange in color and become green in color with development.
5. Freely and continuous flowering habit.
6. Large white-colored flowers that are tinged with light purple with light purple-colored throats.
7. Good garden performance.

Plants of the new *Abelia* can be compared to plants of the female parent, 'Bobbie'. In side-by-side comparisons, plants of the new *Abelia* differ primarily from plants of 'Bobbie' in the following characteristics:

1. Plants of the new *Abelia* are more compact than plants of 'Bobbie'.
2. Plants of the new *Abelia* are denser and more uniformly mounding than and not as open as plants of 'Bobbie'.
3. Developing leaves of plants of the new *Abelia* are brownish orange in color whereas developing leaves of 'Bobbie' are green in color.

Plants of the new *Abelia* can also be compared to plants of *Abelia* x *grandiflora* 'Rika 1', disclosed in U.S. Plant Pat.

No. 20,568. In side-by-side comparisons, plants of the new *Abelia* differ primarily from plants of 'Rika 1' in the following characteristics:

1. Plants of the new *Abelia* are more compact than plants of 'Rika 1'.
2. Plants of the new *Abelia* are denser and more uniformly mounding than and not as open as plants of 'Rika 1'.
3. Developing leaves of plants of the new *Abelia* are more vibrant in color than and not as dull as developing leaves of 'Rika 1'.
4. Plants of the new *Abelia* have larger flowers than plants of 'Rika 1'.
5. Flowers of plants of the new *Abelia* are white in color with light purple-colored throats whereas flowers of plants of 'Rika 1' are pure white in color.

BRIEF DESCRIPTION OF THE PHOTOGRAPHS

The accompanying colored photographs illustrate the overall appearance of the new *Abelia* plant showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet (FIG. 1) is a side perspective view of a typical flowering plant of 'SMNAGBT' grown in an outdoor nursery.

Figure 2:
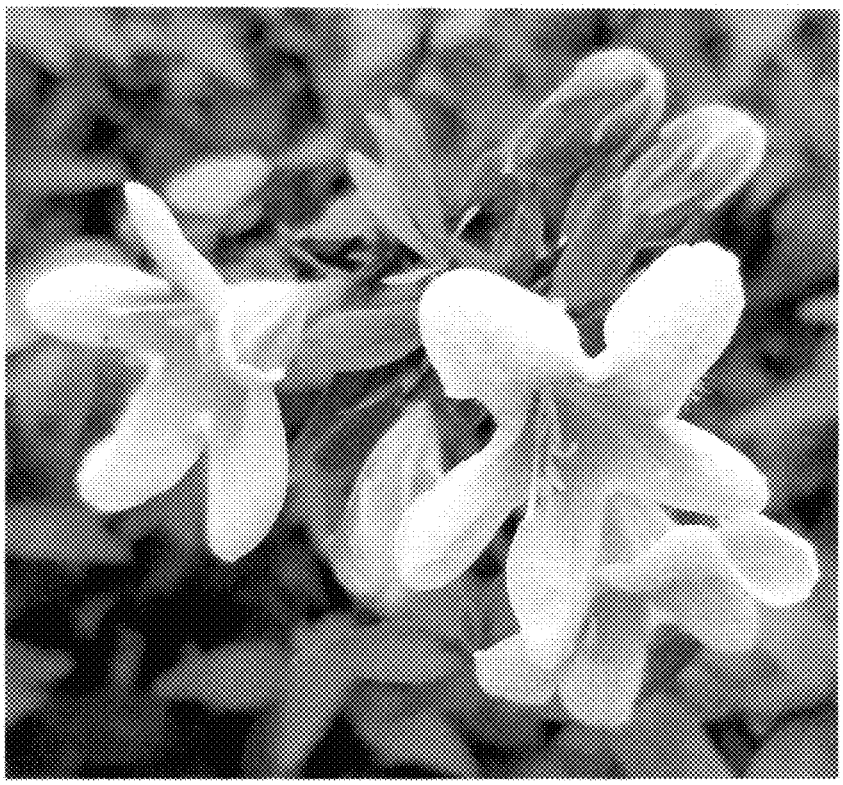

The photograph on the second sheet (FIG. 2) is a close-up view of typical flowers of 'SMNAGBT'.

DETAILED BOTANICAL DESCRIPTION

The following observations, measurements and values describe plants grown during the late summer in three-gallon containers in a polyethylene-covered greenhouse in Grand Haven, Michigan and under cultural practices typical of commercial *Abelia* production. During the production of the plants, day temperatures ranged from 18 C to 27 C and night temperatures ranged from 5 C to 10 C. Plants were four years old when the photographs and the description were taken. In the description, color references are made to The Royal Horticultural Society Colour Chart, 2015 Edition, except where general terms of ordinary dictionary significance are used.

Botanical classification: *Abelia* x *grandiflora* 'SMNAGBT'.

Parentage:

*Female, or seed, parent.*—*Abelia* x *grandiflora* 'Bobbie', not patented.

*Male, or pollen, parent.*—Unknown selection of *Abelia* x *grandiflora*, not patented.

Propagation:

*Type.*—By softwood cuttings.

*Time to initiate roots, summer.*—About one to two months at temperatures ranging from 18 C to 27 C.

*Time to produce a rooted young plant, summer.*—About 40 days at temperatures ranging from 18 C to 27 C.

*Root description.*—Fine, fibrous and fleshy; typically white to tan in color, actual color of the roots is dependent on substrate composition, water quality, fertilizer, substrate temperature and physiological age of roots.

*Rooting habit.*—Freely branching habit; medium density.

Plant description:

*Plant form and growth habit.*—Perennial shrub; relatively compact, upright to outwardly spreading and mounding plant habit; vigorous growth habit and rapid growth rate.

*Branching habit.*—Freely branching habit, dense and bushy growth habit with about 15 to 20 primary lateral branches each with about five to ten secondary lateral branches developing per plant.

*Plant height.*—About 40 cm.

*Plant diameter* (*area of spread*).—About 65 cm.

Lateral branch description:

*Length, primary lateral branches.*—About 35 cm.

*Diameter, primary lateral branches.*—About 5 mm.

*Length, secondary lateral branches.*—About 20 cm.

*Diameter, secondary lateral branches.*—About 1 mm.

*Internode length.*—About 2.5 cm.

*Strength.*—Strong; slightly flexible.

*Aspect.*—About 30 to 80 degrees from vertical.

*Texture, developing.*—Smooth glabrous.

*Texture, fully developed.*—Woody.

*Color, developing.*—Close to N34A.

*Color, fully developed.*—Close to 197B.

Leaf description:

*Arrangement.*—Opposite, simple.

*Length.*—About 3 cm.

*Width.*—About 1 cm.

*Shape.*—Lanceolate.

*Apex.*—Acute to acuminate.

*Base.*—Obtuse.

*Margin.*—Entire; slightly ciliate.

*Texture, upper and lower surfaces.*—Mostly smooth and glabrous with pubescence along margins; slightly asperous.

*Venation pattern.*—Pinnate.

*Color.*—Developing leaves, upper surface: Close to N170A. Developing leaves, lower surface: Close to 182C. Fully expanded leaves, upper surface: Close to between 167B and N167C becoming closer to 146A with development; venation, close to 146D. Fully expanded leaves, lower surface: Close to N170B becoming closer to 146D with development; venation, close to N34A.

*Petioles.*—Length: About 3 mm. Diameter: About 1 mm. Texture, upper and lower surfaces: Smooth, glabrous. Color, upper and lower surfaces: Close to N34A.

Flower description:

*Flower appearance and arrangement.*—Single salverform flowers arranged in terminal clusters; freely flowering habit with about three to six flowers per cluster and numerous flowers developing per plant during the flowering season; flower face upright to mostly outwardly.

*Fragrance.*—Slightly fragrant; sweet and pleasant.

*Natural flowering season.*—Plants flower from July to September in Michigan; flowers not persistent.

*Flower diameter.*—About 2.5 cm.

*Flower depth.*—About 2 cm.

*Flower throat diameter.*—About 7.5 mm.

*Flower tube length.*—About 1.5 cm.

*Flower tube diameter, proximally.*—Close to 2 mm.

*Flower buds.*—Length: About 1 cm. Diameter: Close to 3 mm. Shape: Spatulate. Color: Close to 150D variably tinged with close to N77C.

*Petals*.—Quantity and arrangement: Five fused petals arranged in a single whorl. Lobe length: About 1 cm. Lobe width: About 1 cm. Shape: Elliptic to oblong. Apex: Obtuse. Base: Fused. Margin: Entire. Texture, upper surface: Mostly smooth and glabrous; occasionally, pubescent. Texture, lower surface: Smooth, glabrous; silky. Texture, throat: Mostly smooth and glabrous; occasionally, pubescent. Texture, tube: Smooth, glabrous; silky. Color: When opening and fully opened, upper surface: Close to NN155C variably tinged with close to 76A. When opening and fully opened, lower surface: Close to NN155C. Throat: Close to 76A. Tube: Close to NN155C.

*Sepals*.—Quantity and arrangement: About two to four sepals arranged in a single whorl. Length: About 1 cm. Width: About 3 mm. Shape: Narrowly elliptic to oblong. Apex: Acute. Base: Attenuate. Margin: Entire. Texture, upper and lower surfaces: Smooth, glabrous. Color, upper and lower surfaces: Close to 144B; color becoming closer to 174A after flower senescence.

*Peduncles*.—Length: About 5 mm. Diameter: About 2 mm. Strength: Strong. Aspect: About 45 degrees from stem axis. Texture: Smooth, glabrous. Color: Close to 144B.

*Reproductive organs*.—Stamens: Quantity per flower: Four. Filament length: About 1 cm. Filament color: Close to 155B. Anther length: About 2 mm. Anther shape: Linear. Anther color: Close to 197C. Pollen amount: Sparse to moderate. Pistils: Quantity per flower: One. Pistil length: About 1.5 cm. Stigma shape: Rounded to globose. Stigma color: Close to 155B. Style length: About 1.4 cm. Style color: Close to 155B. Seeds and fruits: To date, seed and fruit production have not been observed on plants of the new *Abelia*.

Garden performance: Plants of the new *Abelia* have been observed to have good garden performance and to tolerate rain, wind and temperatures ranging from about −31 C to about 38 C.

Pathogen & pest resistance: To date, plants of the new *Abelia* have not been shown to be resistant to pathogens and pests common to *Abelia* plants.

It is claimed:

1. A new and distinct *Abelia* plant named 'SMNAGBT' as illustrated and described.

* * * * *